United States Patent [19]

Pearmain

[11] Patent Number: 5,188,839

[45] Date of Patent: Feb. 23, 1993

[54] PHARMACEUTICAL COMPOSITIONS OF CIMETIDINE

[75] Inventor: Kevin E. Pearmain, Hitchin, England

[73] Assignee: Smith Kline & French Laboratories Ltd., Hertfordshire, United Kingdom

[21] Appl. No.: 295,190

[22] PCT Filed: May 4, 1988

[86] PCT No.: PCT/GB88/00349

§ 371 Date: Jan. 4, 1989

§ 102(e) Date: Jan. 4, 1989

[87] PCT Pub. No.: WO88/08703

PCT Pub. Date: Nov. 17, 1988

[30] Foreign Application Priority Data

May 8, 1987 [GB] United Kingdom ............... 8710965
May 8, 1987 [GB] United Kingdom ............... 8710966

[51] Int. Cl.$^5$ .......................... A61K 9/16; A61K 9/20
[52] U.S. Cl. .................................. 424/464; 424/465; 424/466; 424/486; 424/487; 424/489; 514/925; 514/960; 514/961; 514/772.3; 514/779
[58] Field of Search ............... 424/489, 487, 486, 490, 424/464, 690, 692; 514/400

[56] References Cited

U.S. PATENT DOCUMENTS

| | | | |
|---|---|---|---|
| 4,101,651 | 7/1978 | Kobayashi et al. | 424/78 |
| 4,777,033 | 10/1988 | Ikura et al. | 424/81 X |
| 4,800,087 | 1/1989 | Mehta | 424/497 |
| 4,824,664 | 4/1989 | Tarral et al. | 424/439 X |
| 4,892,740 | 1/1990 | Takasima et al. | 424/497 X |

FOREIGN PATENT DOCUMENTS

55-67375 5/1980 Japan.
1539076 1/1979 United Kingdom.

OTHER PUBLICATIONS

Remington's Pharmaceutical Suences, 17th Edition, p. 1296.
Rohm Pharma GmbH, Eudragit E 30 D Technical Application Pamphlet (Info ED-11/e).
Rohm Pharma GmbH, Eudragit L 30 D Technical Application Pamphlet (Info LD-11/e).
Journal of Microencapsulation, vol. 2, No. 3, (London, GB), S. Benita et al., pp. 207-222.
Drug Development and Industrial Pharmacy, vol. 5, No. 2, 1979 (New York, US) G. S. Leonard et al., pp. 217-226.
Scientia Pharmaceutica, vol. 51, 1983 (Vienna, AT), P. Spiegl et al., pp. 215-218.
Chemical Abstracts, vol. 103, 1985 (Columbus, Ohio, US), H. M. El-Sabbagh et al., Abstract No. 76207p.
Rohm Pharma GmbH, Eudragit RL 12,5 Data Sheet (Info RL-2/e).
Rohm Pharma GmbH, Eudragit RL 100 Data Sheet (Info RL-3/e).
Rohm Pharma GmbH, Eudragit RS 12,5 Data Sheet (Info RS-2/e).
K. Lehmann, Acta. Pharm. Fenn. 93, 55-74, (1984) Formulation of Controlled Release Tablets with Acylic Resins.
Rohm Pharma GmbH, Eudragit E 100 Data Sheet (Info E-3/e), 2 pp.
Rohm Pharma GmbH, Eudragit E Standards Sheet (Info E-7/e), 2 pp.
Rohm Pharma GmbH, Eudragit E Technical Application Pamphlet (Info E-13/e) 3 pp.
Rohm Pharma GmbH, Eudragit E Technical Application Pamphlet-I (Info E-12/3) 2 p.
Rohm Pharma GmbH, Eudragit E Technical Application Pamphlet-II (Info E-12/e) 2 pp.
Rohm Pharma GmbH, Eudragit E Technical Application Pamphlet (Info E-11/e) 2 p.
Rohm Pharma GmbH, Eudragit E 12,5 Data Sheet (Info E-2/e) 2 pp.

*Primary Examiner*—Thurman K. Page
*Assistant Examiner*—James M. Spear
*Attorney, Agent, or Firm*—Dara L. Dinner; Stuart R. Suter; Edward T. Lentz

[57] ABSTRACT

The invention provides a pharmaceutical granule comprising cimetidine and 2-20% (w/w) relative to the cimetidine of a co-polymer of dimethylaminoethylmethacrylate and neutral methacrylic acid esters. Compositions of this invention have good palatability and dissolution characteristics.

5 Claims, No Drawings

PHARMACEUTICAL COMPOSITIONS OF CIMETIDINE

This invention relates to granules of cimetidine which are useful in the preparation of tablets and which have an improved flavour.

Cimetidine is a histamine $H_2$-antagonist. It has been described in U.K. Patent Specification 1,397,436. Cimetidine has been shown to be useful in the treatment of duodenal, gastric, recurrent and stomach ulceration, and reflux oesophagitis and in the management of Patients who are at high risk from haemorrhage of the upper gastrointestinal tract.

Cimetidine is known to have a pronounced bitter taste. This is not usually a problem when the dosage form employed is a capsule or a tablet designed to be swallowed, thereafter to disintegrate upon reaching the stomach. However, such dosage forms can be impractical when it is desired to administer a large amount of active ingredient, or to co-administer a relatively bulky second active ingredient such as an antacid or alginate. Moreover many individuals have difficulty in swallowing a solid dosage form.

A conventional approach to administering relatively large amounts of active ingredient in a solid dosage form is by means of a chewable tablet, i.e. a tablet which disintegrates in the mouth upon being chewed. Such a tablet also circumvents the problem of a solid dosage being difficult to swallow.

It will be appreciated that a ma)or requirement of such a dosage form is that it must be palatable, since an unpalatable formulation increases the risk of a patient neglecting to take the tablet. Such non-compliance with the dosing regimen will in turn delay or prevent the patient's recovery from the condition under treatment.

A further requirement of such a composition is that once the disintegrated tablet reaches the stomach, the individual particles should release the active ingredient rapidly and completely in order to ensure that substantially all of the active ingredient is absorbed; that is to say the formulation should be bioavailable.

In the case of cimetidine, because of its bitterness, the provision of such a dosage form represents a considerable problem.

Several solutions to the problem of the bitterness of cimetidine have been proposed. One proposal is disclosed in Japanese patent Application No. 67375/80 wherein there are described granules of cimetidine containing ethylcellulose preferably in the range of 15 to 85% (w/w) and particularly 50% (w/w) relative to the cimetidine. Such granules are described as having good stability to light, good dissolution characteristics and are stated not to have a bitter taste. These properties are stated to be specific to granules containing ethylcellulose; it is disclosed that methylcellulose does not impart such properties.

Another proposed solution is disclosed in Japanese Patent Application No. 86228/78 which similarly describes cimetidine granules containing a specific polymeric substance; in this case polyvinylacetal diethylaminoacetate. The particular granules exemplified in the specification of JP 86228/78 are characterised by having a high sugar content (approximately 75% by weight of the granules), and it is noteworthy that, of all those granules for which test results are provided in the specification demonstrating acceptable solubility and palatability characteristics, all contain approximately 75% by weight of granulated sugar (i.e. presumably sucrose).

Although both JP 67375/80 and JP 86228/78 address the problem of the bitterness of cimetidine, in neither case is it suggested that the granules described therein would be suitable for preparing chewable tablets. In the case of the granules disclosed in JP 86228/78, the use of a high loading of sucrose would be expected to be disadvantageous in a chewable dosage form in view of the well known ability of sucrose to promote tooth decay.

As far as we are aware, up until the time of the making of the present invention, no chewable tablets containing cimetidine have been marketed, or marketed to any significant extent, even though cimetidine per se has been on the market for approximately ten years, and is a well established drug.

Thus it is clear that there remains a need for a cimetidine solid dosage form such as a chewable tablet which is both palatable and allows efficient release of the cimetidine in the stomach.

It has now surprisingly been found that by granulating cimetidine with a particular amount of a particular polymethacrylate co-polymer, a granule is formed which is palatable and which has good dissolution characteristics in the stomach, that is to say, it releases the cimetidine rapidly and completely. Such a granule is particularly useful in the preparation of chewable tablets.

In a first aspect. therefore, the present invention provides a pharmaceutical granule comprising cimetidine and 2-20% (w/w) relative to the cimetidine of a co-polymer of dimethylaminoethylmethacrylate and neutral methacrylic acid esters.

It is preferred that the co-polymer should be present in an amount of approximately 5-15% (W/W) relative to the cimetidine and most preferably it is present in an amount of approximately 10% (w/w).

A co-polymer of the type suitable for use in the present invention is Eudragit E which is manufactured and marketed by Röhm-Pharma of Darmstadt.

In addition to the good palatability and good dissolution characteristics of the granules of the present invention, a further advantage is that they do not need to contain a high loading of sugar, and typically they contain no sugar at all. It is preferred that the granules consist essentially only of cimetidine and the co-polymer.

The granules of the present invention typically are prepared by a wet-granulation method wherein a solution to the Eudragit E in a suitable solvent, for example dichloromethane, is added to the cimetidine and the resulting mixture is blended to form granules. The solvent is lost through evaporation during the granulation step and the subsequent drying step. It will be appreciated that in such a method, the Eudragit is acting as a granulating agent.

Alternatively, the polymethacrylate co-polymer can be used as a coating agent rather than as a granulating agent. In such a case, the cimetidine can be granulated in conventional fashion, for example by using a conventional binding agent such as polyvinylpyrrolidone (PVP); the resulting granules then being coated with the polymethacrylate co-polymer according to known methods. Such methods include tumbling the granules in a coating pan with a solution of the co-polymer or spraying a solution of the co-polymer onto the granules in a fluidised bed apparatus.

Preferably the granules are free of fine powder and aggregates; that is, before compression, the granules will pass through a 1.4 mm sieve and be retained by a 0.2 mm sieve.

The granules of the present invention are particularly suitable for use in chewable tablets and thus chewable tablets containing such granules represent a preferred aspect of the invention.

The tablets of this invention contain normally at least 75 mg of cimetidine. As a maximum the tablet will not normally contain more than 800 mg of cimetidine. Preferably it contains 100 or 200 mg of cimetidine.

The tablets of the invention can also contain a hydroxide or carbonate antacid. Examples of suitable antacids include aluminium hydroxide, magnesium hydroxide, magnesium carbonate, calcium carbonate and co-dried gels for example aluminium hydroxide-magnesium carbonate co-dried gel. In practice the quantity of antacid is between 5 milliequivalents per tablet and 30 milliequivalents, typically approximately 14 milliequivalents.

The tablets can also contain solid diluents such as sugars and sugar alcohols, for example lactose, xylitol, sorbitol and mannitol. Where desired additional sweeteners can be added, for example ammonium qlycyrrhizinate, sodium cyclamate and sodium saccharinate as well as flavours and taste maskers, for example sodium chloride and Contramarum, and tableting starch, which gives the tablets a palatable texture.

The tablets can also contain other standard tableting excipients for example a disintegrant such as a cross-linked polymeric disintegrant; particular examples being cross-linked polyvinyl pyrrolidone and cross-linked carboxymethyl celluloses.

Where the tablet contains an antacid, preferably the antacid is pre-compressed or granulated before it is mixed with the cimetidine granules, for example as described in a co-pending application (reference 11939) deriving priority from British patent application No. 8710965, and as described in the Examples 4 and 5 of this application.

The granules can be sieved to remove fine particles and larger particles, preferably the granules pass through a 1.4 mm sieve but are retained by a 0.2 mm sieve.

The antacid can be pre-compressed or granulated by standard methods.

Tablets prepared according to the present invention can also contain alginate. The purpose of the alginate is to form a raft of mucilage which can float on the gastric contents to prevent reflux oesophagitis.

Typically the alginate is in the form of alginic acid and in such cases the tablet usually also contains a carbonate salt such as sodium bicarbonate to react with the alginic acid to form an alginate salt and liberate carbon dioxide. The liberated gas is dispersed and entrapped in the mucilage thus increasing the volume of the mucilage and decreasing the density.

Alginic acid is a polyuronic acid composed of residues of D-mannuronic and L-guluronic acids. It is a natural product extracted from selected seaweeds, and therefore is subject to some variation in composition and purity. Various grades of alginic acid are available which vary in the proportions of mannuronic and guluronic acid monomers. It is preferred that high guluronic grades are used in the tablets of the present invention since they form a viscous gel in acid media, as opposed to high mannuronic grades which form very weak gels.

The following Examples illustrate the invention.

EXAMPLE 1

Cimetidine 100 mg Chewable Tablet

| Premix Granules | mg/tablet | % w/w |
|---|---|---|
| Cimetidine | 100 | 90.9 |
| Eudragit E100* | 10 | 9.1 |

| Chewable Tablet | mg/tablet |
|---|---|
| Premix Granules | 110.0 |
| Direct Compression Grade Sorbitol | 790.0 |
| Direct Compression Grade Lactoses: | |
| Crystalline | 500.0 |
| Spray dried | 500.0 |
| Croscarmellose Sodium TyPe A | 60.0 |
| Sodium Saccharin (Dried Fine Powder) | 2.0 |
| Aspartame | 2.0 |
| Flavourings | 16.0 |
| Magnesium Stearate | 45.0 |
| TOTAL: | 2,025.0 |

*Added as a 40% w/v solution in Dichloromethane

EXAMPLE 2

Cimetidine 200 mg Chewable Tablet

| Premix Granules | mg/tablet | % w/w |
|---|---|---|
| Cimetidine | 200 | 90.9 |
| Eudragit E100* | 20 | 9.1 |

| Chewable Tablet | mg/tablet |
|---|---|
| Premix Granules | 220.0 |
| Direct Compression Grade Sorbitol | 790.0 |
| Direct Compression Grade Lactoses: | |
| Crystalline | 450.0 |
| Spray dried | 450.0 |
| Croscarmellose Sodium Type A | 60.0 |
| Sodium Saccharin (Dried Fine Powder) | 10.0 |
| Aspartame | 1.0 |
| Flavourings | 17.5 |
| Magnesium Stearate | 45.0 |
| TOTAL: | 2,043.5 |

*Added as a 40% w/v solution in Dichloromethane

The formulations of Examples 1 and 2 were prepared as follows:

The cimetidine was wet-granulated with a solution of the Eudragit E100 in dichloromethane and the resulting granules were dried in a suitable drier and then screened through a 1.4 mm mesh screen. The granules were then blended with the remaining ingredients and the resulting mixture was compressed to form tablets.

EXAMPLE 3

Cimetidine/Alginate Tablet

| | mg/tablet |
|---|---|
| Active constituents | |
| Cimetidine | 200.0 |
| Alginic acid | 500.0 |
| Other constituents | |
| Sodium Bicarbonate | 170 |
| Eudragit E100 | 20 |
| Sorbitol | 680 |
| Pregelatinised Starch | 30 |
| Croscarmellose Sodium Type A | 60 |
| Lactose | 330 |
| Aspartame | 5 |
| Sodium Saccharin | 5 |
| Magnesium Stearate | 35* |

-continued

| | mg/tablet |
|---|---|
| Flavourings | 50 |

*A range of 15 to 35 mg of magnesium stearate may be used.

The cimetidine was granulated with a 40% w/v solution of Eudragit E100 in dichloromethane. The lactose was wet granulated with half the alginic acid, using pregelatinised starch as a binder. After granulation, the granules were dried using either a fluid bed drier or a tray drier. The tablet blend was prepared by mixing together the two component granulations with the remainder of the materials in a planetary mixer or other suitable equipment, and the resulting blend was compressed using a rotary tablet machine.

EXAMPLE 4

100 mg Chewable Tablet

| Ingredient | mg/tablet | |
|---|---|---|
| Clmetidine Premix Granules | | |
| Cimetidine | 100.0 | |
| Eudragit E100* | 10.0 | 110.0 |
| Extragranular | | |
| Aspartame | 3.0 | |
| Peppermint | 15.0 | |
| Tutti Frutti | 5.0 | |
| Spearmint | 5.0 | |
| Lactose | 200.0 | |
| Croscarmellose Sodium Type A | 30.0 | |
| Magnesium Stearate | 15.0 | 273.0 |
| Antacid Granulation: | | |
| Direct Compression Sorbitol | 590.0 | |
| Direct Compression Lactose | | |
| Crystalline | 325.0 | |
| Spray dried | 325.0 | |
| Croscarmellose Sodium Type A | 30.0 | |
| Dried Aluminium Hydroxide Gel** | 250.0 | |
| Magnesium Hydroxide** | 200.0 | |
| Magnesium Stearate | 15.0 | 1735.0 |
| | 2118.0 | 2118.0 |

*Added to the cimetidine by granulation as a 40% w/v solution in methylene chloride. Solvent lost in processing.
**Quantities used adjusted for the potencies of raw materials: Standard quantity of Dried Aluminium Hydroxide gel is equivalent to 117.5 mg/tablet Al₂O₃ or 180 mg/tablet Aluminium Hydroxide (Al(OH)₃).

Process Description

A 40% w/v solution of the Eudragit E100 in methylene chloride is added with mixing to the cimetidine and blended until granules are formed. The resulting granules are dried and then sieved through a 16 mesh screen.

The aluminium hydroxide, magnesium hydroxide and other ingredients for the antacid granules are sieved through a 12 mesh (1.4 mm) screen and mixed together. The resulting mix is compressed on a rotary tablet press and the resulting compacts are milled using a 12 mesh screen.

The cimetidine granules, antacid granules and extragranular excipients are Put into a cone blender and mixed thoroughly. The resulting mix is discharged from the blender and compressed on a suitable rotary tablet press fitted with the appropriate punches.

EXAMPLE 5

200 mg Chewable Tablet

| Ingredient | mg/tablet | % w/w |
|---|---|---|
| Cimetidine Premix Granules | | |
| Cimetidine | 200.0 | 90.9 |
| Eudragit E100* | 20.0 | 9.1 |
| Antacid (Al/Mg) Granules | | |
| Sorbitol: Direct Compression Grade | 295.0 | 34.01 |
| Lactose: Direct Compression Grade | | |
| Spray dried | 162.5 | 18.73 |
| Crystalline | 162.5 | 18.73 |
| Dried Aluminium Hydroxide Gel | 125.0 | 14.41 |
| Magnesium Hydroxide | 100.0 | 11.53 |
| Croscarmellose Sodium Type A | 15.0 | 1.73 |
| Magnesium Stearate | 7.5 | 0.86 |
| | 867.5 | 100.00 |
| Tableting Mix for Compression | | |
| Cimetidine Premix Granules | 220.0 | |
| Antacid (Al/Mg) Granules | 867.5 | |
| Dried Aluminium Hydroxide Gel | 125.0 | |
| Magnesium Hydroxide | 100.0 | |
| Sorbitol: Direct Compression Grade | 295.0 | |
| Lactose: Direct Compression Grade | | |
| Spray dried | 162.5 | |
| Crystalline | 162.5 | |
| Croscarmellose Sodium Type A | 45.0 | |
| Aspartame | 3.0 | |
| Aniseed | 20.0 | |
| Butterscotch | 20.0 | |
| Magnesium Stearate | 22.5 or | 37.5 |
| TOTAL | 2048.0 | 2063.0 |

*Added to the cimetidine by granulation as a 40% w/v solution in methylene chloride. Solvent lost in processing.

Process Description

The cimetidine premix granules and antacid granules were prepared according to the method described in Example 1 The cimetidine granules and antacid granules were then blended with the remaining ingredients and compressed on a rotary press fitted with the appropriate tablet punches and dies.

I claim:

1. A solid pharmaceutical dosage form comprising pharmaceutical granules which comprise an effective amount of cimetidine and about 2-20% w/w relative to the cimetidine of a co-polymer of dimethylaminoethylmethacrylate and neutral methacrylic acid esters wherein the co-polymer functions as a granulating and binding agent and is in admixture with the cimetidine and wherein the granules are compressed into a tablet.

2. The dosage form according to claim 1 wherein the co-polymer is present in an amount of approximately 5-15% (w/w) relative to the cimetidine.

3. The dosage form according to claim 1 wherein the co-polymer is present in an amount of approximately 10% (w/w).

4. The dosage form according to claim 1 which further comprises antacids.

5. The dosage form according to claim 1 which further comprises alginates.

* * * * *